(12) United States Patent
Provonchee

(10) Patent No.: US 12,115,273 B2
(45) Date of Patent: Oct. 15, 2024

(54) AGAROID COMPOSITIONS AND METHODS OF USE THEREOF

(71) Applicant: Advanced Aesthetic Technologies, Inc., Brookline, MA (US)

(72) Inventor: Richard Provonchee, Cushing, ME (US)

(73) Assignee: ADVANCED AESTHETIC TECHMOLOGIES, INC., Brookline, MA (US)

( * ) Notice: Subject to any disclaimer, the term of this patent is extended or adjusted under 35 U.S.C. 154(b) by 0 days.

(21) Appl. No.: 16/320,754

(22) PCT Filed: Apr. 7, 2017

(86) PCT No.: PCT/US2017/026527
§ 371 (c)(1),
(2) Date: Jan. 25, 2019

(87) PCT Pub. No.: WO2018/026400
PCT Pub. Date: Feb. 8, 2018

(65) Prior Publication Data
US 2019/0160200 A1 May 30, 2019

Related U.S. Application Data

(60) Provisional application No. 62/369,256, filed on Aug. 1, 2016.

(51) Int. Cl.
| | | |
|---|---|---|
| A61L 26/00 | (2006.01) | |
| A61F 13/00 | (2006.01) | |
| A61K 47/10 | (2017.01) | |
| A61K 47/36 | (2006.01) | |
| A61L 15/28 | (2006.01) | |
| A61L 15/44 | (2006.01) | |
| A61L 15/60 | (2006.01) | |
| A61L 27/26 | (2006.01) | |

(52) U.S. Cl.
CPC .... *A61L 26/0023* (2013.01); *A61F 13/00063* (2013.01); *A61K 47/10* (2013.01); *A61K 47/36* (2013.01); *A61L 15/28* (2013.01); *A61L 15/44* (2013.01); *A61L 15/60* (2013.01); *A61L 26/0066* (2013.01); *A61L 26/008* (2013.01); *A61L 27/26* (2013.01)

(58) Field of Classification Search
CPC ............. A61L 26/0023; A61L 26/0066; A61L 26/008; A61L 27/26; A61F 13/00063; A61K 47/10; A61K 47/36
See application file for complete search history.

(56) References Cited

U.S. PATENT DOCUMENTS

| | | |
|---|---|---|
| 3,335,127 A | 8/1967 | Polson |
| 4,291,025 A | 9/1981 | Pellico |
| 5,965,070 A | 10/1999 | Provonchee |
| 2002/0128579 A1 | 9/2002 | Church |
| 2011/0027340 A1 | 2/2011 | King |
| 2013/0017232 A1 | 1/2013 | Varghese et al. |
| 2014/0271757 A1 | 9/2014 | Agrawal et al. |
| 2014/0377195 A1* | 12/2014 | Cabrera ................ A61K 47/10 424/58 |
| 2015/0182559 A1 | 7/2015 | Masinaei et al. |

\* cited by examiner

*Primary Examiner* — Robert S Cabral
(74) *Attorney, Agent, or Firm* — WOMBLE BOND DICKINSON (US) LLP; Deborah M. Vernon; Ricardo Joseph

(57) ABSTRACT

Provided herein are therapeutic and cosmetic methods that utilize an in situ gelling agaroid composition in the form of a water reactive agaroid. The composition described herein is applicable in the fields of wound healing, tissue bulking, bone grafting, and drug delivery.

7 Claims, No Drawings

AGAROID COMPOSITIONS AND METHODS OF USE THEREOF

BACKGROUND

Agaroids are widely available and biocompatible compositions known for their gelling properties. Such compositions have significant potential to be used in therapeutic and cosmetic applications, though compositions utilizing agaroids frequently suffer from non-ideal melting and gelling properties as well as high viscosities.

Specifically, agaroids have a large temperature differential between their melting and gelling temperatures—commonly referred to as thermal hysteresis. The melting temperature and the dissolution temperature of an agaroid are similar enough that for the purpose of this discussion, they are considered essentially the same. Most agaroids have a gelling temperature between about 25° C. and 50° C. while having a melting temperature between about 70° C. and 100° C. This thermal hysteresis in the liquid-gel transition creates significant barriers to using agaroids for in-situ gelling therapeutic or cosmetic applications.

In order for an agaroid composition to gel in-situ, it must be made from an agaroid that will gel at the temperature of the application site or, if not, the application site must be cooled to below the gelling temperature of the agaroid. The agaroid composition must be applied as a liquid or a semi-gel and form the desired gel properties after application. This means that the agaroid composition must generally be at a temperature above its gelling temperature prior to and during its application, and then cooled to below its gelling temperature after application. One way to accomplish this is by melting or dissolving the agaroid composition and then allowing it to cool to a predetermined temperature just above its gelling temperature and holding it at this temperature until application. Although this may not appear to be a cumbersome procedure in a laboratory setting, real-world applications in a doctor's office, hospital, or other clinical setting requires precision heating and cooling equipment not usually found in these settings, and requires significant time to carry out the heating and cooling steps. While this procedure may be cumbersome in the above mentioned clinical settings, it becomes prohibitive in non-clinical settings such as in the field or in emergency situations. Moreover, because of the thermal hysteresis of agaroids, if at any time prior to application the agaroid composition falls below its gelling temperature, it will need to be reheated to above its melting temperature and cooled again to just above its gelling temperature prior application.

Another limitation of agaroids is the rate at which the viscosity of a solution rises with increasing agaroid content. Solutions with agaroid content greater than about 4% (w/v) become difficult to handle due to their viscosity.

Therefore, there is a need to develop biocompatible agaroid compositions that gel at body temperatures, can be stored a room temperatures and do not require significant heating and subsequent cooling prior to use in or on a mammalian body and that can be used at higher concentrations without significant viscosity increase. Such compositions should be applicable in wound healing, dermal filling, bone grafting, hemostasis, and other therapeutic and cosmetic technologies.

SUMMARY

The term "Water Reactive Agaroid" (WRA) as used herein refers to an agaroid composition that will form a thermo-reversible agaroid gel on exposure to an aqueous environment when both the agaroid composition and the aqueous environment are at temperatures below the gelling temperature of any resultant gel.

In certain embodiments, the invention relates to methods of forming a gel in or on a mammalian body, comprising contacting a mammalian body with a composition comprising a WRA, thereby forming a gel in or on a mammalian body.

In another aspect, the invention provides methods of treating a wound or skin injury in a subject, comprising topically administering to the subject at the wound or skin injury a composition comprising a WRA.

In another aspect, the invention provides methods of stabilizing a bone supplement at a bone void or bone graft site, comprising: contacting a bone supplement with a composition comprising a WRA to form a WRA-bone supplement mixture; and contacting the bone void or bone graft site with the WRA-bone supplement mixture.

In other aspects, the invention provides methods of topically administering an active pharmaceutical ingredient to a subject, comprising contacting the subject with a composition comprising the active pharmaceutical ingredient and a WRA.

In further aspects, the invention provides methods of filling or bulking a soft tissue in a subject, the method comprising administering to the soft tissue a composition comprising a WRA.

In other aspects, the invention provides methods of implanting an active pharmaceutical ingredient to a target site in a subject, comprising delivering to the target site a composition comprising the active pharmaceutical ingredient and a WRA.

In further aspects, the invention features WRA compositions comprising an agaroid, glycerin and a glycol.

In another aspect, the invention features WRA compositions comprising an agaroid, glycerin, a glycol and water.

DETAILED DESCRIPTION

WRA

The WRA compositions described herein are a solid, a liquid solution or suspension, or a semi-gelled solution or suspension or a combination thereof at temperatures below the gelling temperatures of any resultant gels, and form a gel when exposed to water at a temperature below the gelling temperature of the resultant gel.

Some of the WRA compositions used in the methods of the invention are solutions that comprise an agaroid and glycerin, or an agaroid and glycerin and a glycol, or an agaroid and glycerin and a glycol and water. Some of the WRA compositions used in the methods of the invention comprise an agaroid precipitated from a glycol solution and are herein referred to as 'WRA solid'. Preferably, the agaroid composition forms a gel when exposed to water at a temperature below the gelling temperature of the resultant mixture.

In-situ gelation is essentially a process of gel formation at the site of application after the composition or formulation has been applied to the site. In the field of human and animal medicine, the sites of application may refer to various injection sites, topical application sites, surgical sites, and others where the agents are brought into contact with tissues or body fluids.

In certain embodiments, on exposure to water the WRAs will gel at a temperature at or above body temperature (37° C.). In certain embodiments, on exposure to water the WRAs will gel at a temperature below body temperature (<37° C.). The gelling temperature may be dependent upon the agaroid used. For example, an agaroid made from Gracilaria seaweed is an example of an agaroid that typically gives a WRA with a gelling temperature above body temperature when exposed to water. In contrast, an agaroid made from Gelidium seaweed typically yields a WRA with a gelling temperature below body temperature when exposed to water. Accordingly, agaroids with a gelling temperature above 37° C. are the preferred agaroids to be used in the invention. Although the gelling temperature of an agaroid can be raised by methods familiar to persons of ordinary skill in the art, agaroids derived from Gracilaria seaweed typically have gelling temperatures that are above 37° C.

Typically, the WRA gels upon exposure to water. In certain embodiments, minimal water is required to initiate the gelling. For example, in certain embodiments, water vapor from the air will cause the WRA to gel. Alternatively, a WRA can gel upon exposure to bodily fluids at body temperature.

Agaroids useful in this invention may include, but are not limited to, one or more crude, purified, or modified agars or agaroses. For example, in certain embodiments, the agaroid is selected from agar, agarose, purified agarose, and derivatized agarose. The agaroids may also be used as mixtures with other compatible polymers and additives such as carrageenan, chitosan, alginate, gelatin, hyaluronic acid, collagen. Preferably, the agaroid used in the composition of the invention is agar, agarose, derivatized agar, or derivatized agarose. In certain embodiments, the agaroid is Gracilaria-derived agarose. Gracilaria-derived agarose has a higher methoxy content than agarose derived from other sources (e.g., Gelidium). In certain embodiments, a combination of two or more agaroids may be used. Agaroids from other seaweeds, for example, Pterocladia or Gelidiella may also be used. As used herein, the term 'agaroid' refers to agaroids selected from the group comprising agar, purified agar, agarose, purified agarose, derivatized agar and derivatized agarose.

In certain embodiments, the WRA used in the methods of the invention further includes a glycol. In certain embodiments, the glycol is one or more $C_1$-$C_4$ alkylene glycols, including, but not limited to, ethylene glycol, diethylene glycol, triethylene glycol, trimethylene glycol, propylene glycol, and butylene glycol (1,2-butanediol). It is known in the art that polyethylene glycols, such as triethylene glycol, contain other glycols (e.g. ethylene glycol, diethylene glycol, etc.). In certain embodiments, the glycol is propylene glycol.

In some embodiments, the WRA composition of the invention consists essentially of an agaroid and glycerin.

In further embodiments, the WRA composition consists essentially of an agaroid, glycerin, and a glycol.

In still further embodiments, the WRA composition consists essentially of an agaroid, glycerin, a glycol, and water.

In some embodiments, the WRA composition of the invention consists essentially of an agaroid precipitated from a glycol solution.

In some embodiments, the WRA composition of the invention consists of an agaroid and glycerin.

In further embodiments, the WRA composition consists of an agaroid, glycerin, and a glycol.

In still further embodiments, the WRA composition consists of an agaroid, glycerin, a glycol, and water.

In still further embodiments, the WRA composition of the invention consists of an agaroid precipitated from a glycol solution.

In certain embodiments, the concentration of the agaroid in solution in the WRA composition is about 0.1% to about 10% weight/volume (w/v), about 1% to about 10% w/v, about 0.5% to about 5% w/v, about 1.5% to about 5% w/v, about 2% to about 3% w/v, about 1.5% to about 2.5% w/v, or about 2% w/v.

In certain embodiments, the content of the agaroid precipitated from a glycol in the composition is about 0.1% to about 99% by weight, about 1% to about 60% by weight or about 2% to 4% by weight. In certain embodiments, the content of the agaroid precipitated from a glycol solution can be as high as 100% by weight.

As discussed herein the WRA preferably forms a gel when exposed to water at certain temperatures. Accordingly, as used herein, the term "activated WRA" refers to a WRA that has been exposed to water. In certain embodiments in which the WRA contains water, the term "activated WRA" refers to a WRA that has been exposed to water other than the water that is included in the WRA composition.

As used herein, the term "WRA gelling temperature" refers to the temperature at which or below which the WRA will form a gel when, or after, being exposed to water. In certain embodiments, the WRA composition further comprises water, and the water is present in an amount not more than 15% by volume. In further embodiments, the water is present in an amount not more than 7.5% by volume, or not more than 5% by volume.

In further embodiments, the WRA compositions of the invention comprise an agaroid that has been precipitated from a glycol solution. Such compositions exhibit the qualities of a solid that can dissolve and form a gel when exposed to water at temperatures below the gelling temperature of the resulting gel.

A person of ordinary skill in the art can determine the preferred glycerin to glycol ratio and amount of water, if included, of the WRA based on the application for which the WRA is to be used, the temperature at which the WRA is to be used, and the type and concentration of the agaroid to be used.

The term "water" as used herein may refer to water liquid or vapor, water in combination with water-soluble and -insoluble materials, or water contained in bodily fluids.

A person of ordinary skill in the art can readily determine the preferred agaroid concentration in a WRA based on the desired application or based on its anticipated mode of delivery. For example, if a soft gel or gel-like material is desirable, the agaroid concentration may be lower relative to a WRA that is to be used if a firm gel or gel-like material is desirable. Similarly, if the WRA solution is to be administered through a small-bore needle, the agaroid concentration will typically be lower than if the WRA solution is to be administered through a large-bore needle or otherwise administered via a means in which low viscosity is not a requirement.

The gelling rate of the WRA composition can be altered by, for example, raising or lowering the temperature of the WRA composition prior to injection. The range of temperatures allowed is limited by the temperature tolerance of the target site. Alternatively, the gelling rate of the WRA can be altered by localized warming or cooling of the target site before, during, or after injection.

In some embodiments, the WRA composition is activated by mixing the WRA composition with water or an aqueous solution prior to contact in or on a mammalian body, wherein during and after mixing, the mixture is at a temperature above the WRA composition gelling temperature. The mixing can be accomplished by any reasonable means including but not limited to stirring, shaking, passing through a static mixer, transferring between two syringes. In embodiments in which the mixture is above the WRA gelling temperature, there is no rush to introduce the mixture to the target site. If a gelled or semi-gelled mixture is preferred for injection or other application, the mixture can be cooled with or without further manipulation prior to introducing the mixture to the target site.

Alternatively, the WRA composition is activated by mixing the WRA composition with water or an aqueous solution prior to contact in or on a mammalian body, wherein during and after mixing, the mixture is at a temperature below the WRA gelling temperature. The mixing can be accomplished by any reasonable means including but not limited to stirring, shaking, passing through a static mixer, transferring between two syringes. In embodiments in which the mixture is below the WRA gelling temperature, the mixture is preferably introduced to the target site quickly after mixing, such that the mixture is closer to a liquid state. If a gelled or semi-gelled mixture is preferred for injection or other application, more time is available between mixing and injection.

Methods of Making the WRA

The WRA compositions described herein may be produced by a number of methods that would be understood by a person of ordinary skill in the art. Typically these methods include dispersing the agaroid in one or more solvents and heating with mixing to dissolve the agaroid. For example, to make a WRA composition, an agaroid may be dissolved in (a) glycerin; (b) glycerin and water; (c) glycerin and glycol; or (d) glycerin, glycol, and water. For example, to make a WRA solid composition an agaroid may be dissolved in (a) glycol with heat; or (b) glycol and water with heat and on cooling, the WRA solid will precipitate out of the solution.

In certain embodiments, the agaroid is dissolved in the one or more solvents at an elevated temperature, optionally with mixing. The elevated temperature may be about 50°-150° C., or preferably about 80°-110° C. In certain embodiments, excessively high dissolution temperatures, e.g., above 150° C., may degrade the agaroid and/or other components.

The WRA may be manufactured in a batch-wise, semi-continuous, or continuous manner.

Once it has been produced, the WRA may be stored in a manner to protect against exposure to water or moisture.

Properties of the WRA

The WRA compositions of the invention are bio-compatible and easy to manufacture. Typically, the WRA compositions used in the invention are liquid phase solutions or suspensions at body temperatures and temperatures below body temperatures. WRA compositions used in the invention may also be powders or pastes. When exposed to water, the WRA compositions form a gel having the melting and gelling properties similar to the constituent agaroid. Thus, the WRA gel will not return to the liquid phase until heated to temperatures well above body temperature.

The water that can initiate the WRA gelling may be water liquid or vapor, or may be water in a bodily fluid. For example, the WRA may gel on contact with a bodily fluid at human body temperatures.

Before use, some of the WRA compositions used in the methods of the invention may be cooled (e.g., after its production at elevated temperatures). This may cause thickening of the WRA mixture.

Alternatively, before use, some of the WRA compositions used in the methods of the invention may be heated or warmed. For example, warming the WRA composition may liquefy a partially gelled or soft gel composition and may reduce the viscosity.

Preferably, the WRA compositions of the invention are able to liquefy at or below about 50° C.

In certain embodiments, WRA compositions comprising a glycol do not gel at room temperature. In alternative embodiments, WRA compositions comprising a glycol create weak gels at room temperature, such that the weak gels will liquefy at 50° C. or below. Depending on the components of the WRA mixture, the presence of glycol can cause some of the agarose to precipitate out of solution, thereby forming a cloudy solution and lowering the viscosity of the mixture. This precipitation can be advantageous because the agarose that precipitates does not contribute to the overall viscosity of the composition but still contributes to the overall agaroid content. It is advantageous in these cases to have the composition form a weak gel at room temperature thereby inhibiting the settling of the precipitated agaroid during storage.

As will be detailed herein, the special gelling properties of the WRA enable its application to many therapeutic and cosmetic methods, such as dermal filling, bone grafting, hemostasis, wound care, tissue engineering, food applications, and so forth.

WRA Solid

Further agaroid compositions described herein relate to agaroids precipitated from a glycol solution. These compositions are referred to herein as "WRA solid", which term refers to agaroids precipitated from a glycol solution that will dissolve and form a gel when exposed to water at temperatures below the gelling temperature of the resulting gel.

In certain embodiments, the WRA solid will gel at a temperature at or above body temperature (37° C.). In certain embodiments, the WRA solid will gel at a temperature below body temperature (<37° C.).

Typically, the WRA solid gels upon exposure to water. In certain embodiments, minimal water is required to initiate the gelling. For example, in certain embodiments, water vapor from the air will cause the WRA solid to gel. Alternatively, a WRA solid can gel upon exposure to bodily fluids at body temperature.

In certain embodiments, the WRA solid used in the methods of the invention comprises an agaroid precipitated from a glycol (e.g., a glycol solution). Accordingly, in certain embodiments, the WRA solid further comprises a glycol.

The term "WRA solid in the form of a suspension" as used herein refers to particles of WRA solid in a non-aqueous non-solvent, including, for example, a slurry.

The term "WRA solid in the form of a particulate solid" as used herein refers to WRA solid in an essentially dry form. For example, the particulate solid from may be a powder, larger dry or damp particulates, or a paste form. If there is a liquid component, it is a non-aqueous non-solvent.

The term "WRA solid matrix or mat" as used herein refers to WRA solid in a three-dimensional porous form.

The term "activated WRA solid" as used herein refers to WRA solid that has been exposed to water.

In certain embodiments, the glycol from which the agaroid is precipitated is one or more $C_1$-$C_4$ alkylene glycols, including, but not limited to, ethylene glycol, diethylene glycol, triethylene glycol, trimethylene glycol, propylene glycol, and butylene glycol (1,2-butanediol). It is known in the art that polyethylene glycols, such as triethylene glycol, contain other glycols (e.g. ethylene glycol, diethylene glycol, etc.). In certain embodiments, the glycol is propylene glycol.

In certain embodiments, the content of the agaroid precipitated from a glycol solution in the WRA solid composition is about 0.1% to about 99% by weight, about 1% to about 60% by weight or about 2% to 4% by weight. In certain embodiments, the content of the WRA solid precipitated from a glycol solution can be as high as 100% by weight.

In certain embodiments, the glycol solution from which the WRA solid is precipitated further comprises water, and the water is present in an amount not more than 15% by weight, or not more than 10% by weight. In certain embodiments, the water is present in the glycol solution in an amount of about 0.5% to about 10% by weight.

In certain embodiments, the WRA solid composition comprises an agaroid precipitated from a glycol solution in the form of a powder.

In certain embodiments, the WRA solid composition comprises an agaroid precipitated from a glycol solution in a porous three dimensional form.

In certain embodiments, the WRA solid composition comprises an agaroid precipitated from a glycol solution in the form of a suspension.

In certain embodiments, the WRA solid composition comprises an agaroid precipitated from a glycol solution in the form of a suspension in a water miscible non-solvent.

In certain embodiments, the WRA solid composition comprises an agaroid precipitated from a glycol solution in the form of a suspension in a water immiscible non-solvent.

In certain embodiments, the WRA solid composition comprises an agaroid precipitated from a glycol solution in the form of a paste.

In certain embodiments, the WRA solid composition comprises an agaroid precipitated from a glycol solution in the form of a paste made with a water miscible non-solvent.

In certain embodiments, the WRA solid composition comprises an agaroid precipitated from a glycol solution in the form of a paste made with a water immiscible non-solvent.

Methods of Making WRA Solid

Throughout this disclosure, the term "source agaroid" is intended to cover any of the agaroids described herein, including agarose and agar.

In certain embodiments, a WRA solid is prepared by dissolving an agaroid in a lower alkylene glycol at elevated temperature, cooling the agaroid-containing glycol solution to induce precipitation of a WRA solid product, and recovering the precipitated WRA solid product. In certain embodiments, the alkylene glycol is selected from ethylene glycol, diethylene glycol, propylene glycol and trimethylene glycol.

In certain embodiments, the glycol solution contains a small amount of water, e.g., less than about 15 wt % water, and more preferably within the range of 0.5-10 wt % water. In certain such embodiments, the glycol is propylene glycol or diethylene glycol. When the glycol used to dissolve the agaroid is substantially water-free, the glycol is preferably ethylene glycol or trimethylene glycol.

Dissolution of the agaroid in the glycol is preferably carried out at a temperature of about 50° C. to about 130° C., more preferably 80° C. to about 110° C. when the glycol is ethylene glycol or propylene glycol.

The source agaroid is preferably in particulate form, e.g., a powder, but flake material or the like may also be used. It is not necessary that the source agaroid be dry. Wet material in the form of a coagulum or wet cake, which contains moisture, alcohol, or other glycol-soluble liquid from previous processing steps, may be employed.

The glycols suitable for use in this invention are lower alkylene glycols. Suitable lower alkylene glycols include ethylene glycol (1,2-ethanediol), diethylene glycol, propylene glycol (1,2-propanediol) and trimethylene glycol (1,3-propanediol). Other lower glycols may be workable under certain conditions; 1,2-butanediol will dissolve the source agaroid provided that small amounts of water are present, in the glycol.

Mixtures of these lower alkylene glycols may also be employed. Mixtures of lower alkylene glycols, e.g., ethylene glycol and propylene glycol containing equal parts of each glycol component, give satisfactory results. Other components or additives may also be present in the glycol if desired, e.g., salts such as sodium chloride or sodium acetate. Such additives may be used to increase the WRA solid product recovery yield.

Water, in small amounts, may also be present in the glycol used to dissolve the source agaroid. In certain such embodiments, the aqueous glycol should contain less than about 25 wt % water, less than 15 wt % water, and most preferably in the range of 0.5-10 wt % water.

With ethylene glycol or trimethylene glycol, the source agaroid readily dissolves in the glycol. Such glycols are desirably used in pure form, being substantially water-free. In contrast, with propylene glycol or diethylene glycol as the selected glycol, dissolution of the source agaroid is enhanced by the presence of small amounts of water in the glycol. The aqueous glycol should contain less than 15 wt % water and preferably contains from about 0.5-10 wt % water.

Dissolution of the source agaroid is carried out at elevated temperature. The glycol may be heated to the desired dissolution temperature before, during, or after addition of the source agaroid. The dissolution temperature is preferably within the range of about 50° C. to about 130° C. Excessively high dissolution temperatures, e.g., above 150° C., are best avoided because the agaroid may be degraded by exposure to such high temperatures. When the specified glycol is ethylene glycol or propylene glycol, dissolution is desirably carried out at a temperature of about 80° C. to about 120° C.

In certain embodiments, the source agaroid is preferably added gradually to the glycol, to promote rapid dissolution of the agaroid without clumping. The length of time for the source agaroid to dissolve will depend on the method of addition, on the sizing of the material, on the source agaroid itself, and on the dissolution temperature chosen. Dissolution rate is increased, all other factors being equal, with small particle sizing, so powdered or particulate source agaroid is preferred over flaked material but flaked material may be used without deviating from the invention. Agitation or vigorous mixing of the source agaroid in the glycol is also helpful in promoting more rapid dissolution. Higher dissolution temperatures, within the above-noted ranges, usually enhance the dissolution rate.

Once the source agaroid has been completely dissolved, the agaroid containing solution is cooled to induce precipitation of the WRA solid product. There is no need for a holding period at the elevated dissolution temperature, and cooling may be begun immediately after complete dissolution has been achieved.

If cooling is accompanied by mixing, the WRA solid product will typically precipitate as a finely-divided material. If cooling is allowed to take place without mixing, the WRA solid product will typically precipitate as a porous three dimensional form. Rapid cooling with mixing typically creates a rough surfaced precipitate with high surface area while slow cooling with mixing typically creates a smooth surfaced spheroid-like precipitate. The solution should be cooled to a temperature below about 70° C., preferably below about 50 ° C. and most preferably below about 30° C.

The precipitated WRA solid product may be used as is in the glycol slurry or may be recovered from the glycol slurry by conventional means. The precipitate is typically a finely-divided material that may be separated from the glycol solution via filtration, centrifugation, or the like.

The precipitated WRA solid product may be washed, during its recovery, with a volatile organic solvent that is miscible with the glycol and that is a non-solvent for the agaroid. The solvent is preferably a lower alkyl alcohol and is preferably selected from methanol, ethanol or isopropanol. The solvent may also be acetone.

The method of this invention may be carried out either batchwise, semicontinuously, or continuously.

WRA Compositions

Certain WRA compositions are better suited to certain applications while other WRA compositions are somewhat less suited to certain applications. For example, a WRA composition made from an agaroid dissolved in glycerin with or without additional water may, over time, spontaneously form a gel without being exposed to additional water. In certain applications, this spontaneous gelling may cause shelf life limitations. For another example, a WRA composition made from an agaroid precipitated from a glycol solution and suspended in a non-aqueous non-solvent may settle over time. In certain applications, this settling may cause a mixing requirement before use. While the above two examples exemplify WRA compositions that may have drawbacks in certain applications, the WRA compositions exemplified have significant value with regard to the methods described herein.

It has been found that the possible drawbacks exemplified above can be ameliorated by using glycerin and a glycol in certain ratios with or without the addition of small amounts of water.

When a WRA comprising an agaroid and glycerin further comprises a glycol, the tendency of the composition to spontaneously gel can be reduced.

When a WRA composition made from an agaroid precipitated from a glycol solution further comprises glycerin, the tendency to settle can be reduced.

Glycerin to glycol ratios in the WRA compositions in the range from about 100 to 0 to about 0 to 100, with or without the inclusion of small amounts of water, have proven to be useful with regard to the methods described herein.

Glycerin to glycol ratios in the WRA compositions in the range from about 95 to 5 to about 35 to 65, with or without the inclusion of small amounts of water, have proven to be particularly useful with regard to some of the methods described herein.

For any given application, the optimal glycerin to glycol ratio, and the amount of water if included, depend on the application, the type of agaroid used, the concentration of the agaroid used, the temperature of storage, the temperature of use, and the method of use. With the information provided herein, a person of ordinary skill in the art can arrive at an appropriate glycerin to glycol ratio, with the inclusion of water, if any, that will provide a WRA composition with useful properties.

WRA Pharmaceutical Compositions

In certain embodiments, the WRA compositions used in the methods of the invention are topical compositions.

In certain embodiments, the composition is in a form suitable for topical administration. The composition can also be present in a transdermal delivery system, e.g., a skin patch. The topically applicable form of the composition can be a transdermal patch, ointment, cream, gel, suspension, liquid, elixir, or eye drop.

In certain embodiments, the topical compositions of the invention may include one or more pharmaceutically active agents, therapeutic agents or cosmetic compositions.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration.

In some embodiments, the WRA pharmaceutical compositions described herein are suitable for administration to the mouth, e.g., buccal administration, may be presented as a mouthwash, an oral spray, or an oral ointment.

Dosage forms for the topical or transdermal administration include powders, sprays, ointments, pastes, creams, lotions, gels, solutions, patches, bandages, inhalants, mouthwash, eye drops, and intranasal droplets.

In any of the applications detailed herein, if it is beneficial to include with the WRA a therapeutic or cosmetic composition that contains enough water to compromise the desired properties of the WRA, that therapeutic or cosmetic composition can be isolated from the WRA by coating or encapsulation or other means known in the art.

Gel Formation using WRA

In certain embodiments, the invention relates to a method of forming a gel in or on a mammalian body, comprising contacting a mammalian body with a composition comprising a WRA, thereby forming a gel in or on a mammalian body.

In certain embodiments, the gel provides a therapeutic or cosmetic benefit to the mammalian body.

In certain embodiments, the agaroid used in the composition is selected from agar, agarose, purified agarose, and derivatized agarose.

In certain embodiments, the composition further comprises a glycol. The glycol may be selected from ethylene glycol, diethylene glycol, triethylene glycol, trimethylene glycol, propylene glycol, and butylene glycol. In certain preferred embodiments, the glycol is propylene glycol.

In certain embodiments, the concentration of the agaroid in the composition is about 0.1% to about 10% weight/volume (w/v), about 1% to about 10% w/v, about 0.5% to about 5% w/v, about 1.5% to about 5% w/v, about 2% to about 3% w/v, about 1.5% to about 2.5% w/v, or about 2% w/v.

In certain embodiments, the content of the agaroid precipitated from a glycol in the composition is about 0.1% to about 99% by weight, about 1% to about 60% by weight or about 2% to 4% by weight. In certain embodiments, the content of the agaroid precipitated from a glycol solution can be as high as 100% by weight.

In certain embodiments, the composition further comprises water, and the water is present in an amount not more than 15% by volume, or not more than 5% by volume.

In certain embodiments, the step of contacting a mammalian body occurs at a dermal region on the mammalian body. The dermal region may be affected by a scar, wrinkle, blemish, void, or volumetric weakening.

Alternatively, the step of contacting a mammalian body can occur at a bone, bone graft, or bone supplement in the mammalian body.

In further alternative embodiments, the step of contacting a mammalian body occurs at a site of active bleeding.

In further alternative embodiments, the step of contacting a mammalian body occurs at a wound.

Wound Treatment

The gelling properties of the WRA compositions are useful in the field of wound treatment. Upon gelling on a wound surface or other tissue injury, the WRA compositions provide a form-filling and fitting gel surface that maintains intimate contact with the wound surface while providing an appropriately moist environment for tissue regeneration. Moreover, the gelled WRA compositions can absorb and contain exudates from the wound. The gelled WRA composition benefits the wound by not permitting the wound to dry out, thus preventing the bandage or wound dressing from becoming bonded to the wound or the surrounding tissue. Because a moist environment is maintained, removal of the wound dressing does not damage the wound bed or peri-wound.

Accordingly, in some aspects, the invention described herein provides a method of treating a wound or skin injury in a subject, comprising topically administering to the subject at the wound or skin injury a composition comprising a WRA. The term "wound" as used herein refers to all types of tissue injuries, including those inflicted by surgery and trauma, including burns, as well as injuries from chronic medical conditions, such as atherosclerosis, vascular disease, or diabetes. The WRA compositions described herein are useful for treatment of all types of wounds, including wounds to internal and external tissues. The wound dressings are intended to treat the various etiologies of wounds that affect the three layers of the skin—the epidermis, dermis, and subcutaneous layers.

In certain embodiments, the agaroid used in the composition is selected from agar, agarose, purified agarose, and derivatized agarose.

In certain embodiments, the composition further comprises a glycol. The glycol may be selected from ethylene glycol, diethylene glycol, triethylene glycol, trimethylene glycol, propylene glycol, and butylene glycol. In certain preferred embodiments, the glycol is propylene glycol.

In certain embodiments, the concentration of the agaroid in the composition is about 0.1% to about 10% weight/volume (w/v), about 1% to about 10% w/v, about 0.5% to about 5% w/v, about 1.5% to about 5% w/v, about 2% to about 3% w/v, about 1.5% to about 2.5% w/v, or about 2% w/v.

In certain embodiments, the content of the agaroid precipitated from a glycol in the composition is about 0.1% to about 99% by weight, about 1% to about 60% by weight or about 2% to 4% by weight. In certain embodiments, the content of the agaroid precipitated from a glycol solution can be as high as 100% by weight.

In certain embodiments, the composition further comprises water, and the water is present in an amount not more than 10% by volume, or not more than 5% by volume.

In certain embodiments, the composition used in the treatment of wounds or skin injuries further comprises a therapeutic agent selected from a group including topical steroids, retinoids, antimicrobial agents, coagulation agents, analgesics, and anesthetics. Preferably, the therapeutic agent is selected from antimicrobial agents, coagulation agents, analgesics, and anesthetics.

In some embodiments, the composition is administered as an ointment, liquid, gel, lotion, spray, paste, or foam, or is incorporated into or deposited on a bandage or compress.

The viscosity of the WRA composition should be suitable for the delivery method. The viscosity should be controlled so that the composition can be applied to the wound in a way that a conformal WRA gel dressing is generated. Viscosity can be controlled by altering, e.g., the type or concentration of the agaroid, glycerin, or the glycol. Viscosity can also be controlled, preferably lowered, by including agaroid precipitated from a glycol solution in the composition. Alternatively, it can be controlled by altering the temperature or water content of the WRA composition.

It should be understood that desired characteristics of a WRA gel dressing will vary depending upon the intended usage of the dressing—such as where it will be applied, what type of wound is being treated, and other factors.

The WRA dressing should be conformable and compliant so that it conforms to the topography of the wound and the tissue surface around the wound and is comfortable to wear. Conformability will also extend the longevity of the dressing. The WRA dressing is also preferably strong enough that it can be peeled off the wound without reinjuring the wound bed and can be removed in one cohesive unit leaving little material behind in the wound bed. In some cases it is desirable to debride the wound in order to enhance overall healing. In other cases debridement is not desirable. The amount of debridement facilitated by the WRA dressing is, in part, dependent on the degree to which the gel adheres to the wound surface. Thus, it is often desirable to control the adhesion and surface tackiness of the dressing by the inclusion of one or more additives.

In certain embodiments, the wound or skin injury is a pressure sore, burn, cancer wound, ulcer, surgical site, dermatology wound, traumatic wound, diabetic wound, chronic wound, or acute wound.

Alternatively, the wound or skin injury may be a site of active bleeding.

In some embodiments, application of the WRA composition to a wound reduces the formation or appearance of a scar.

Application of the WRA composition to a wound has other therapeutic effects such as elimination of strong odors, conservation of living fat cells, and cessation and reversal of hypergranulation.

The WRA composition used in the methods of treating a wound or skin injury described herein preferably gels upon contact with the wound. To facilitate the gelling of the WRA, the method may further comprise the step of wetting the composition with water prior to topically administering the composition. In such embodiments, the WRA composition is applied to the wound site after it has gelled or partially gelled. Alternatively, the method may further comprise wetting the composition with water after topically administering the composition. In yet further embodiments, the water that initiates gelling of the WRA can be supplied by the wound itself.

In preferred embodiments, the WRA composition forms a gel upon contact with the wound or skin injury.

By gelling upon application of the dressing, the method of treating a wound or skin injury is fast, clean, "touchless" (hands free) and simple. The WRA composition can be applied to any size or type of wound using the same "touchless" delivery device, thereby reducing the need to prepare various sizes of pre-formed wound dressings. Because it forms in situ, the gel dressing is highly conformal to the wound which ensures that the active agents are more efficiently delivered directly to the wound site. Meanwhile, penetration of the gel into the wound bed may aid in debridement of the wound during dressing changes without removal of epithelial cells, which is known to accelerate the wound healing process.

In certain embodiments, the wound or skin injury is a site of active bleeding. In such embodiments, the WRA composition of the invention can have a hemostatic effect on the bleed site.

In certain embodiments, the invention provides a method for slowing or stopping the flow of blood, comprising applying a WRA composition described herein to a site of blood flow. Upon application to the bleed site, the WRA composition gels, thereby slowing or stopping the flow of blood. The WRA composition can be activated by water in the blood or any other bodily fluid that may be present. In certain embodiments, additional water may be added to the WRA composition at the site of the blood flow in order to enhance the gelling rate. The WRA composition can be applied to the site by itself or it can be incorporated into a bandage or compress or the like. Alternatively, the WRA composition can be applied to the bleed site in the form of a spray or a foam.

In certain embodiments, the invention provides a method for slowing or stopping the flow of blood, comprising applying a WRA solid composition described herein to a site of blood flow. Upon application to the bleed site, the WRA solid composition dissolves and gels, thereby slowing or stopping the flow of blood. The WRA solid composition can be activated by water in the blood or any other bodily fluid that may be present. In certain embodiments, additional water may be added to the WRA solid composition at the site of the blood flow in order to enhance the gelling rate. The WRA solid composition can be applied to the site by itself or it can be incorporated into a bandage or compress or the like. Alternatively, the WRA composition can be applied to the bleed site in the form of a spray or a foam.

In further embodiments, the WRA composition that is used in a hemostatic application further comprises one or more materials that improve the hemostatic function of the WRA composition. Such materials include, but are not limited to, medicinal or therapeutic agents, pain reducing agents, or coagulation inducing agents. The coagulation inducing agent may be selected from thrombin, a snake venom, a platelet activator, a thrombin receptor activating peptide, and a fibrinogen precipitating agent.

Bone Graft Applications

The gelling properties of the WRA compositions described herein are also applicable in the field of bone grafting and bone void filling, and other bone supplement therapies.

Bone supplements are used to correct surgical defects that may be caused by trauma, pathological disease, surgical intervention or other situations where defects need to be managed, for example, in osseous surgery. Bone supplements also find utility in filling defects or voids in bone material, or retaining a bone graft material in a desired position.

The special gelling properties of the WRA compositions described herein render the composition useful to stabilize a bone supplement within its target site, conferring positional stability to the bone supplement and the surrounding tissue. The combined WRA composition and bone supplement material are conformable to the surgical site or bone graft site, which site is often uneven in shape or depth. Moreover, the components of the WRA composition enhance cell proliferation, migration, and adhesion.

In certain aspects, the invention provides a method of stabilizing a bone supplement at a bone void or bone graft site, comprising: contacting a bone supplement with a composition comprising a WRA to form a WRA-bone supplement mixture; and contacting the bone void or bone graft site with the WRA-bone supplement mixture.

The term "bone supplement" as used herein refers to materials that encourage, enhance, promote, or initiate bone growth, regrowth or grafting. Bone supplement materials are known in the art and may be solids (e.g., powders) or liquids, or a combination thereof.

The term "stabilizing" as used herein with reference to bone supplements refers to increasing the retention of the bone supplement in a target site. Retention of a bone supplement may be enhanced by binding a particulate bone supplement into a more cohesive mass, by improving adhesiveness, by providing a matrix for the controlled delivery of the bone supplement, or any combination thereof.

In certain embodiments, the agaroid used in the bone-stabilizing WRA composition is selected from agar, agarose, purified agarose, and derivatized agarose.

In certain embodiments, the WRA composition is in the form of a solution or of a liquid suspension or a combination thereof. In certain embodiments, the WRA composition is in the form of paste. In certain embodiments, the WRA is in the form of a powder.

In certain embodiments, the composition further comprises a glycol. The glycol may be selected from ethylene glycol, diethylene glycol, triethylene glycol, trimethylene glycol, propylene glycol, and butylene glycol. In certain preferred embodiments, the glycol is propylene glycol.

In certain embodiments, the concentration of the agaroid in the composition is about 0.1% to about 10% weight/volume (w/v), about 1% to about 10% w/v, about 0.5% to about 5% w/v, about 1.5% to about 5% w/v, about 2% to about 3% w/v, about 1.5% to about 2.5% w/v, or about 2% w/v.

In certain embodiments, the content of the agaroid precipitated from a glycol in the composition is about 0.1% to about 99% by weight, about 1% to about 60% by weight or about 2% to 4% by weight. In certain embodiments, the content of the agaroid precipitated from a glycol solution can be as high as 100% by weight.

In certain embodiments, the composition further comprises water, and the water is present in an amount not more than 10% by volume, or not more than 5% by volume.

Preferably, after the step of contacting the bone void or bone graft site with the WRA-bone supplement mixture, the mixture gels from exposure to water. This gelling act serves to stabilize the bone supplement material. The water may be applied to the WRA-bone supplement mixture at the bone void or bone graft site, or alternatively, the water may be supplied by the site itself.

Accordingly, in certain embodiments, the method further comprises wetting the WRA-bone supplement mixture with water prior to contacting the bone void or bone graft site.

In alternative embodiments, the method further comprises wetting the WRA-bone supplement mixture with water after contacting the bone void or bone graft site.

In certain embodiments, the step of contacting the bone void or bone graft site with the WRA-bone supplement mixture occurs in vivo.

In certain embodiments, the WRA-bone supplement mixture is injected into a subject (e.g., through a needle), thereby contacting the bone void or bone graft site.

In certain embodiments, the WRA composition described herein may be used in contact with bleeding bone. This condition is created either from trauma or a surgical procedure that may involve drilling, sawing, grinding or scraping the bone to achieve a bleeding condition. In surgery, the bone is traumatized or surgically cut exposing blood capillaries, Haversian canals (micro-channels in the bone), periosteum (the protective tissue lining around bone), muscle and other structures in the surgical site. The WRA composition in combination with the bone supplement material serves as an osteoconductive matrix and also signals the patient's tissue and cells to initiate the growth of new bone (osteoinduction).

The WRA composition may include one or more additional active and non-active materials that can enhance stabilization of the bone supplement. These materials may be included with the WRA to reduce discomfort to the patient, increase the radio opacity, improve imaging contrast, introduce medicinal or therapeutic agents to the target site, or improve the handling of the composition. Accordingly, in certain embodiments, the composition used in stabilizing a bone supplement at a bone void or bone graft site further comprises an agent selected from the group consisting of imaging contrast agents, analgesics, and anesthetics.

Drug Delivery

The WRA compositions of the invention are also useful for drug delivery applications. The gelling properties of the WRA composition can provide numerous benefits to a drug delivery application, including enhancing the physical stability of the drug delivery composition and altering drug delivery rate.

In certain embodiments, the invention provides a method of topically administering an active pharmaceutical ingredient to a subject, comprising contacting the subject with a composition comprising the active pharmaceutical ingredient and WRA.

In certain embodiments, the agaroid used in the composition is selected from agar, agarose, purified agarose, and derivatized agarose.

In certain embodiments, the composition further comprises a glycol. The glycol may be selected from ethylene glycol, diethylene glycol, triethylene glycol, trimethylene glycol, propylene glycol, and butylene glycol. In certain preferred embodiments, the glycol is propylene glycol.

In certain embodiments, the concentration of the agaroid in the composition is about 0.1% to about 10% weight/volume (w/v), about 1% to about 10% w/v, about 0.5% to about 5% w/v, about 1.5% to about 5% w/v, about 2% to about 3% w/v, about 1.5% to about 2.5% w/v, or about 2% w/v.

In certain embodiments, the content of the agaroid precipitated from a glycol in the composition is about 0.1% to about 99% by weight, about 1% to about 60% by weight or about 2% to 4% by weight. In certain embodiments, the content of the agaroid precipitated from a glycol solution can be as high as 100% by weight.

In certain embodiments, the composition further comprises water, and the water is present in an amount not more than 10% by volume, or not more than 5% by volume.

In certain embodiments, the composition is administered as an ointment, liquid, gel, lotion, spray, paste, or foam, or is incorporated into or deposited on a bandage or compress.

Preferably, the composition comprising the active pharmaceutical ingredient and WRA gels upon topical administration to a subject.

Accordingly, in certain embodiments, the method further comprises wetting the composition with water prior to topically administering the composition. In certain such embodiments, the composition is applied to the administration site after partial gelling.

Alternatively, in certain embodiments, the method further comprises wetting the composition with water after topically administering the composition.

In certain embodiments, the composition comprising the active pharmaceutical ingredient and WRA forms a gel upon contact with the subject.

In certain embodiments, the active pharmaceutical ingredient is selected from topical steroids, retinoids, antimicrobial agents, coagulation agents, analgesics, and anesthetics.

Further drug delivery applications include implantation of drug depot forms using the WRA compositions described herein.

In certain embodiments, drug depot compositions and methods are provided, which can easily allow accurate and precise implantation of a drug depot in situ with minimal physical and psychological trauma to a patient. One advantage of the drug depot compositions and methods is that the drug depot can now be easily delivered to the target site using a flowable composition that gels upon contact with the target site. In this way, accurate and precise implantation of a drug depot in a minimally invasive procedure can be accomplished. Another advantage, in various embodiments, is that by varying the agaroid concentration in the composition, the rate of drug delivery from the drug depot can be adjusted. Raising the agaroid concentration or content typically slows the rate of drug delivery, while lowering the agaroid concentration or content typically increases the rate of drug delivery.

As used herein, the term "target site" includes sites in tissue, organs, body cavities, bone, meninges and spinal column.

In certain embodiments, the invention provides a method of implanting an active pharmaceutical ingredient to a target site in a subject, comprising delivering to the target site a composition comprising the active pharmaceutical ingredient and a WRA.

In certain embodiments, the agaroid used in the composition is selected from agar, agarose, purified agarose, and derivatized agarose.

In certain embodiments, the composition further comprises a glycol. The glycol may be selected from ethylene glycol, diethylene glycol, triethylene glycol, trimethylene glycol, propylene glycol, and butylene glycol. In certain preferred embodiments, the glycol is propylene glycol.

In certain embodiments, the concentration of the agaroid in the composition is about 0.1% to about 10% weight/volume (w/v), about 1% to about 10% w/v, about 0.5% to about 5% w/v, about 1.5% to about 5% w/v, about 2% to about 3% w/v, about 1.5% to about 2.5% w/v, or about 2% w/v.

In certain embodiments, the content of the agaroid precipitated from a glycol in the composition is about 0.1% to about 99% by weight, about 1% to about 60% by weight or about 2% to 4% by weight. In certain embodiments, the content of the agaroid precipitated from a glycol solution can be as high as 100% by weight.

In certain embodiments, the composition further comprises water, and the water is present in an amount not more than 10% by volume, or not more than 5% by volume.

In certain embodiments, the composition is administered as a liquid or a gel.

Preferably, the composition comprising the active pharmaceutical ingredient and WRA gels upon delivery to the target site.

Accordingly, in certain embodiments, the method further comprises wetting the composition with water prior to delivery to the target site. In certain such embodiments, the composition is delivered to the target site after partial gelling.

Alternatively, in certain embodiments, the method further comprises wetting the composition with water after the composition is delivered to the target site.

In certain embodiments, the composition comprising the active pharmaceutical ingredient, a WRA forms a gel upon contact with the target site.

Dermal Filler and Tissue Bulking

The WRA compositions described herein may also be utilized in applications for filling or bulking the soft tissue. Such applications may be cosmetic or therapeutic. The special gelling characteristics of the WRA enable it to be applied to a subject (e.g., injected into a subject) in a liquid form. After application, the WRA gels, effectively "filling" the space in which it is applied.

As used herein, the terms "tissue filling" and "tissue bulking" and "filling or bulking soft tissue" include aesthetic smoothing and bulking of the skin, filling scars, filling voids in skin and tissue, or creating masses in tissue or body voids. The term "dermal filling" may also be used to describe this process.

The WRA for dermal filling or tissue bulking can be introduced to the target site in a number of ways including intradermally or subcutaneously, or the composition can be implanted or applied topically.

In certain embodiments, the invention provides a method of filling or bulking a soft tissue in a subject, the method comprising administering to the soft tissue a composition comprising a WRA. In certain embodiments, the agaroid used in the composition is selected from agar, agarose, purified agarose, and derivatized agarose.

In certain embodiments, the composition further comprises a glycol. The glycol may be selected from ethylene glycol, diethylene glycol, triethylene glycol, trimethylene glycol, propylene glycol, and butylene glycol. In certain preferred embodiments, the glycol is propylene glycol.

In certain embodiments, the concentration of the agaroid in the composition is about 0.1% to about 10% weight/volume (w/v), about 1% to about 10% w/v, about 0.5% to about 5% w/v, about 1.5% to about 5% w/v, about 2% to about 3% w/v, about 1.5% to about 2.5% w/v, or about 2% w/v.

In certain embodiments, the content of the agaroid precipitated from a glycol in the composition is about 0.1% to about 99% by weight, about 1% to about 60% by weight or about 2% to 4% by weight. In certain embodiments, the content of the agaroid precipitated from a glycol solution can be as high as 100% by weight.

In certain embodiments, the composition further comprises water, and the water is present in an amount not more than 10% by volume, or not more than 5% by volume.

In certain embodiments, the WRA composition of the invention is used as a dermal filler, and may be injected into a tissue (e.g., the skin) of a subject. Once at the target site, the WRA preferably gels from exposure to water, which may be applied to the WRA prior to the injection, at the injection site or may be naturally supplied by the site, or a combination thereof. The injected WRA can be passively left to gel or can be manipulated during the gelling process.

The gelling rate of the WRA composition can be altered by, for example, raising or lowering the temperature of the WRA composition prior to injection. The range of temperatures allowed is limited by the temperature tolerance of the target site. Alternatively, the gelling rate of the WRA can be altered by localized warming or cooling of the target site before, during, or after injection.

In some embodiments, the WRA composition is activated by mixing the WRA composition with water or an aqueous solution, wherein during and after mixing, the mixture is at a temperature above the WRA composition gelling temperature. The mixing can be accomplished by any reasonable means including but not limited to stirring, shaking, passing through a static mixer, transferring between two syringes. In embodiments in which the mixture is above the WRA gelling temperature, there is no rush to introduce the mixture to the target site. If a gelled or semi-gelled mixture is preferred for injection or other application, the mixture can be cooled with or without further manipulation prior to introducing the mixture to the target site.

Alternatively, the WRA composition is activated by mixing the WRA composition with water or an aqueous solution, wherein during and after mixing, the mixture is at a temperature below the WRA gelling temperature. The mixing can be accomplished by any reasonable means including but not limited to stirring, shaking, passing through a static mixer, transferring between two syringes. In embodiments in which the mixture is below the WRA gelling temperature, the mixture is preferably injected quickly after mixing, such that the mixture is closer to a liquid state. If a gelled or semi-gelled mixture is preferred for injection or other application, more time is available between mixing and injection.

In some embodiments, the composition further comprises an agent selected from the group consisting of imaging contrast agents, radio-opaque agents, pigmentation agents, anti-pigmentation agents, moisturizing agents, tensioning agents, anti-acne agents, antioxidants, anti-itch agents, anti-cellulite agent, anti-scarring agents, anti-inflammatory agents, analgesics, and anesthetics.

In some embodiments, the method of tissue bulking further comprises wetting the composition with water prior to administering the composition to the soft tissue.

Alternatively, the method of tissue bulking further comprises wetting the soft tissue with water.

In certain embodiments, the soft tissue is the dermal region, and the method treats skin defects including wrinkles, scars, or blemishes.

Emboli

The special gelling properties of the WRA composition described herein, particularly its ability to gel on exposure to blood, makes the composition a candidate for creating emboli. In certain embodiments, the WRA composition may be combined with a material that swells on contact with blood, such that the mixture provides sufficient blocking functionality or binding functionality.

The WRA composition can also be combined with a substance that generates a gas on contact with water (e.g., combined sodium bicarbonate and anhydrous citric acid) and when exposed to blood, the WRA composition will activate and gel in concert with gas being generated. This process creates bubbles trapped in a gel, and thereby improves the emboli functionality.

WRA Foam

The WRA compositions described herein can be formulated as a foam by any number of methods known to a person of ordinary skill in the art. In certain embodiments, the invention provides methods of formulating the WRA composition as a foam, further comprising the step of contacting the foam with water. As a result, the water causes the WRA foam to gel, which sets the foam with no additional steps required. In certain embodiments, the foam is formed at a temperature above the WRA gelling temperature, such that the WRA will not gel and set the foam until the foam is cooled to below the gelling temperature of the activated WRA. Alternatively, the WRA can be exposed to water during the process of foam creation. Alternatively, the foam can be brought into contact with water after the foam is manufactured. The foam can be created and used immediately or created and stored in the wet state for use at a later time or dried and used at a later time.

Having now described aspects of the invention in detail, the same will be more clearly understood by reference to the following examples, which are included herewith for purposes of illustration only and are not intended to be limiting of the invention

EXAMPLES

Materials, Methods, and General Remarks

The experiments outlined herein utilize agarose derived from Gracilaria (HGT agarose, Lonza, Rockland, Me. USA) and Gelidium (LE agarose, Lonza, Rockland, Me. USA). HGT agarose has a higher gelling temperature (~44° C.) than agarose derived from Gelidium (~34° C.). The higher gelling temperature is particularly advantageous when working with body temperatures (37° C.). The higher gel temperature is the result of agarose from Gracilaria having a higher methoxy content.

Dissolution temperatures used in the experiments outlined herein were in the 120-140° C. range. Room temperature (RT) indicates a temperature of about 15° C.

Though a number of glycols are suitable for the WRA compositions described herein, the following experiments utilized propylene glycol (PG).

In all examples below, all ingredients were mixed in a suitable sized flask, covered and heated with mixing until all of the ingredients dissolved. Mixtures were cooled by letting the flask stand at RT until equilibrated to RT.

Regardless of form—fluid, semi-gel, soft gel, suspension, sol—the products of all of the examples below form a gel or a more solid gel on exposure to water at RT.

Example 1

100 mL Glycerin//2 g HGT gave a viscous, slightly hazy liquid as it returned to room temperature. After sitting at room temp for a day or so, the material took on weak gel-like qualities.

The composition did not liquefy at 50° C.

Example 2

2 g HGT agarose dissolved in 100 mL glycerin with a water content above 10% gave a solid gel on cooling to RT.

The composition did not liquefy at 50° C.

Example 3

100 mL Glycerin//2 g LE gave a clear liquid at RT that gelled after sitting about a week at RT.

The gel did not melt at 40° C.

Example 4

95 mL Glycerin//5 mL water//2 g HGT gave a viscous, slightly hazy liquid as it returned to room temperature. The viscosity appeared to be somewhat lower than Example 1. After sitting at RT for a day or so, the material took on gel-like qualities that were firmer than with 100% glycerin.

The composition did not liquefy at 50° C.

Example 5

92.5 mL Glycerin//7.5 mL water//2 g HGT gave a semi-solid gel when it cooled to RT.

The composition did not liquefy at 50° C.

Examples 1-5 show some results of dissolving an agaroid in glycerin with and without added water. In all 5 examples, the composition formed a gel after sitting at room temperature for a few days. The addition of small amounts of water appear the make the room temperature formed gel firmer. All of the compositions, once gelled, would not melt at 40° C.

Example 6

90 mL Glycerin//10 mL PG//0 mL water//2 g HGT gave a clear gel at RT.

Hazy viscous liquid with possibly slight gel at 20° C.

Clear viscous liquid at 30° C. and above

Example 6 shows the difference the addition of even a small amount of glycol can make to the behavior of the composition.

Example 7

85 mL Glycerin//10 mL PG//5 mL water//2 gm LE gave a clear liquid at RT.

Example 8

80 mL glycerin//20 mL PG//0 mL water//2 g HGT gave a hazy gel at RT.

Clear viscous liquid at 20° C. and above

Example 9

80 mL Glycerin//20 mL PG//0 mL water//2 g LE gave a hazy liquid at RT.

Clear viscous liquid at 20° C. and above

Examples 8 and 9 show the difference the gelling temperature of the source agaroid can have on the room temperature characteristics of the resultant compositions.

Example 10

80 mL Glycerin//20 mL EG//0 mL water//2 g HGT gave a hazy gel at RT.

Soft clear gel at 40° C.

Example 11

75 mL Glycerin//20 mL PG//5 mL water//2 g HGT gave a clear semi-gelled solution at RT.

Clear fluid at 30° C.—somewhat thick.

Clear fluid at 40° C.—slightly more viscous that Example 19.

Example 12

75 mL Glycerin//20 mL PG//5 mL water//4 g HGT gave a clear semi-gelled solution at RT.

Example 13

75 mL Glycerin//20 mL PG//5 mL water//2 gm LE gave a slightly hazy liquid at RT.

Example 14

75 mL glycerin//25 mL PG//0 mL water//1 g HGT was cloudy and gelatinous at RT.
Clear viscous liquid at 40° C. and above

Example 15

75 mL glycerin//25 mL PG//5 mL water//1 g HGT was a clear weak gel at RT Clear viscous liquid with a grainy gel texture at 40° C.
Examples 14 and 15 show the difference a small amount of water can make in the appearance of the composition at room temperature and the texture at 40° C. when the glycerin to glycol ratio is about 75 to 25.

Example 16

70 mL Glycerin//30 mL PG//0 mL water//2 g HGT was cloudy and slightly gelatinous at RT.
Cloudy viscous liquid at 20° C.
Clear viscous liquid at 30° C. and above

Example 17

67 mL Glycerin//28 mL PG//5 mL water//2 g HGT gave a clear viscous solution with a hint of gel at RT.
Clear fluid at 37° C. with slight gel like qualities.
Clear fluid at 40° C.—similar viscosity as Example 21.

Example 18

60 mL Glycerin//40 mL PG//2 g HGT was cloudy and gelatinous at RT.
Cloudy and less gelatinous at 20° C.
Hazy viscous liquid at 30° C.
Clear viscous liquid at 40° and above

Example 19

50 mL Glycerin//50 mL PG//2 g HGT was a cloudy weak gel at RT.
Cloudy weak gel at 20° C.
Cloudy weak gel at 30° C.
Cloudy and gelatinous at 40° C.
Clear and gelatinous at 50° C.
Clear and slightly gelatinous at 60° C.

Example 20

50 mL Glycerin//50 mL PG//2.5 ml water//2 g HGT was a cloudy gelatinous gel at RT.
Less cloudy and gelatinous at 40° C.

Example 21

50 mL Glycerin//50 mL PG//5 ml water//2 g HGT was cloudy with very slight gelling.
Clear viscous liquid at 40° C. and above

Example 22

50 mL Glycerin//50 mL PG//7.5 ml water//2 g HGT was a cloudy gel at RT.
Clear gel at 40° C.
Examples 19-22 show the effect of additional water when the glycerin to glycol ratio is about 50 to 50. Unlike examples 14 and 15 where the glycerin to glycol ratio was 75 to 25 and the added water caused a gel like grainy-ness at 40° C., examples 19-21 show that, to a point, added water improves the liquid qualities of the composition at 40° C. Example 22 shows that too much water can cause gelation.

Example 23

47.5 mL Glycerin//47.5 mL PG//5 mL water//2 g HGT gave a cloudy somewhat gelatinous material at RT.
Cloudy fluid at 30° C.
Clear fluid at 34° C.
Clear fluid at 40° C.

Example 24

40 mL Glycerin//60 mL PG//2 g HGT was a cloudy weak gel at RT
Cloudy weak gel at 20° C.
Cloudy weak gel at 30° C.
Cloudy liquid at 40° C.
Hazy liquid at 50° C.
Clear liquid at 60° C.

Example 25

30 mL Glycerin//70 mL PG//2 g HGT gives very cloudy suspension at RT with evidence of settling after a day or so.
Very cloudy suspension at 20° C. with evidence of settling
Very cloudy suspension at 30° C. with evidence of settling
Very cloudy suspension at 40° C. with evidence of settling
Very cloudy suspension at 50° C. with evidence of settling
Hazy liquid at 60° C. with evidence of settling

Example 26

25 mL Glycerin//60 mL PG//15 mL water//2 g HGT Gave a firm gel at RT. Will not liquefy at 40° C.

Example 27

25 mL Glycerin//75 mL PG//0 mL water//1 g HGT was cloudy suspension with evidence of settling.
Cloudy suspension with evidence of settling at 50 C.

Example 28

25 mL Glycerin//75 mL PG//5 mL water//1 g HGT was a hazy liquid with a settled cake of precipitate after several days at RT.
Clear liquid with settled cake at 50 C.

In all of the examples above, a hazy appearance may be from the agaroid gelling or from some of the agaroid precipitating from solution or a combination thereof whereas a cloudy appearance is likely to be primarily the result of the agaroid precipitating from the solution.

While specific embodiments of the subject invention have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

What is claimed is:
1. A composition of matter comprising a solution comprising:

an agaroid;

glycerin; and a glycol selected from the group consisting of propylene glycol and butylene glycol, wherein the ratio of glycerin to glycol by volume is in the range of 90 to 10 to 50 to 50.

2. The composition of claim 1, wherein the agaroid is selected from the group consisting of agar, agarose, purified agarose, and derivatized agarose.

3. The composition of claim 1, further comprising one or more of a topical steroid, a retinoid, an imaging contrast agent, a radiopaque agent, a pigmentation agent, a tensioning agent, a moisturizing agent, an anti-itch agent, an anti-acne agent, an anti cellulite agent, an anti-scarring agent, an anti-inflammatory agent, an anti-oxidant, an anti microbial agent, a coagulation agent, an analgesic and an anesthetic.

4. The composition of claim 1, wherein the concentration of the agaroid in the composition is about 0.1% to about 10% weight-to-volume.

5. The composition of claim 1, further comprising water in an amount not more than 10% by volume of the composition.

6. The composition of claim 1, wherein the glycol is propylene glycol.

7. The composition of claim 1, wherein the composition forms a gel upon contact with water when the water is in a liquid form or a vapor form.

* * * * *

UNITED STATES PATENT AND TRADEMARK OFFICE
CERTIFICATE OF CORRECTION

| | | |
|---|---|---|
| PATENT NO. | : 12,115,273 B2 | Page 1 of 1 |
| APPLICATION NO. | : 16/320754 | |
| DATED | : October 15, 2024 | |
| INVENTOR(S) | : Provonchee | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 62 days.

Signed and Sealed this
Tenth Day of June, 2025

Coke Morgan Stewart
*Acting Director of the United States Patent and Trademark Office*